United States Patent [19]

Shigemitsu et al.

[11] Patent Number: 5,519,030
[45] Date of Patent: May 21, 1996

[54] METHOD FOR PROPHYLAXIS AND TREATMENT OF MYOPIA

[75] Inventors: Toshiro Shigemitsu, Nagoya; Noriko Watanabe, Suita, both of Japan

[73] Assignee: Senju Pharmaceutical Co., Ltd., Osaka, Japan

[21] Appl. No.: 314,685

[22] Filed: Sep. 29, 1994

[30] Foreign Application Priority Data

Oct. 7, 1993 [JP] Japan .................... 5-251383
Feb. 4, 1994 [JP] Japan .................... 6-012537

[51] Int. Cl.⁶ .................... A61K 31/44
[52] U.S. Cl. .................... 514/291; 514/912
[58] Field of Search .................... 514/291, 912

[56] References Cited

PUBLICATIONS

Abstract of Japanese Journal Nippon Ganka Kiyo (1988), 39(2), 202–10.

*Primary Examiner*—Zohreh Fay
*Attorney, Agent, or Firm*—Wenderoth, Lind & Ponack

[57] ABSTRACT

A method for the prophylaxis and treatment of myopia, comprising administering a compound of the formula

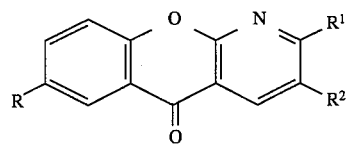

wherein R is an alkyl, $R^1$ is a hydrogen or an amino and $R^2$ is a carboxyl or a tetrazole, or a salt thereof. The method for the prophylaxis and treatment of myopia of the present invention not only shows relaxing action on the ciliary smooth muscle of rabbit, but also shows superior effects of prevention and treatment of myopia of the patients on whom Mydrin-M, a conventional preparation for the prophylaxis and treatment of myopia, failed to have effects. In addition, the method does not involve a mydriatic response and can be advantageously used for the prophylaxis and treatment of myopia.

11 Claims, 4 Drawing Sheets

METHOD FOR PROPHYLAXIS AND TREATMENT OF MYOPIA

TECHNICAL FIELD OF THE INVENTION

The present invention relates to a method for the prophylaxis and treatment of myopia.

BACKGROUND OF THE INVENTION

Myopia is defined as the state wherein parallel rays of light entering the eye are brought to focus before the retina.

Myopia generally includes the following two kinds. One is axial myopia. This is caused by abnormally long axis of the eye when lens power is normal, and severe myopia is often found in this kind. The axial myopia generally starts from infancy and the axis of the eye gradually grows and abnormalities are developed in fundus oculi. Specifically, atrophy of retina and chorioidea, abnormal increase and decrease of pigments, clouding of vitreous body, retinal hemorrhage to result in detachment of the retina and even losing eyesight can be observed.

The other is refractive myopia. This is caused by abnormal curvature of cornea or acquired increase in the thickness of the lens due to reading, close work for the eye such as VDT (visual display terminal) work, etc. to result in too strong a power of cornea and lens. Included therein is pseudomyopia which is caused by unfixed state of continuing and growing contraction of the ciliary smooth muscle. The pseudomyopia is the state of thickened lens in refractive myopia before the instillation of a cycloplegia. After the instillation of a cycloplegia, however, the thickness of the lens becomes less and refractive error shifts toward the hyperopia side by 1 D (diopter) or more.

Clear distinction between these two kinds of myopia (axial myopia and refractive myopia), however, is very difficult to make and the coexistence of the two is said to be frequently seen. At present, it is commonly understood that the close work for the eye is one of the causes of myopia, though the cause of myopia still remains to be clarified. More specifically, when close work for the eye is done, contraction of ciliary smooth muscle makes the lens thicken. Continuation of this state for an extended period of time results in failure to restore to its original state, which in turn causes substrate change of ciliary smooth muscle to result in refractive myopia, which further causes fragile posterior membrane of the eye to permit growing axis of the eye, thus causing axial myopia.

Alternatively, alleviation of the contractile state of ciliary smooth muscle is said to cure myopia. For this end, local administration (instillation) of a drug such as tropicamide is done for alleviating the tension of ciliary smooth muscle. Yet, the efficacy of the drug differs among patients and is not entirely satisfactory. Besides the administration, physical therapy such as low frequency therapy, ultrasonic therapy and training of looking far-off are tried, none of which, however, has achieved satisfactory results.

As described in the above, there is no satisfactory method or composition for the prophylaxis and treatment of myopia. Thus, the strong need remains for the development of a superior composition and a method for the prophylaxis and treatment of myopia in both patients and doctors.

SUMMARY OF THE INVENTION

According to the present invention, it has now been found that the compound of the following formula (I) surprisingly relaxes ciliary smooth muscle, which controls the lens thickness, according to the mechanism different from that of the conventionally-used drug containing tropicamide as an active ingredient, and that this action of the compound exerts superior preventive and therapeutic effects on myopia by restoring the refractive error, which is in the myopic state, to the normal range, which resulted in the completion of the invention.

The compound which is the active ingredient of the composition for the prophylaxis and treatment of myopia of the present invention concurrently has, as described in Japanese Patent Unexamined Publication No. 61-10587, inhibitory action on SRS-A production and antagonistic action against SRS-A, as well as inhibits histamine release due to IgE-mediated allergy and is known to possess strong antiallergic activity and anti inflammatory activity. The present inventors have found for the first time that said compound has superior relaxing action on the contraction of the ciliary smooth muscle, in addition to the action as mentioned above.

Accordingly, the present invention relates to: (1) a method for the prophylaxis and treatment of myopia, comprising administering a compound of the formula

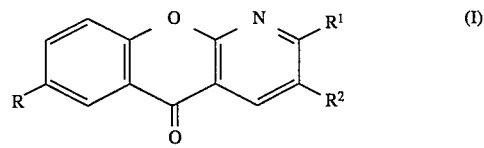

(I)

wherein R is an alkyl, $R^1$ is a hydrogen or an amino and $R^2$ is a carboxyl or a tetrazole, or a salt thereof, (2) the method for the prophylaxis and treatment of myopia as described in (1) above, wherein the alkyl is an isopropyl, (3) the method for the prophylaxis and treatment of myopia as described in (1) above, which is for local administration to the eye, (4) the method for the prophylaxis and treatment of myopia as described in (3) above, which is an eye drop, (5) the method for the prophylaxis and treatment of myopia as described in (4) above, which is an aqueous eye drop, and (6) the method for the prophylaxis and treatment of myopia as described in (5) above, further comprising a solubilizing agent.

DETAILED DESCRIPTION OF THE INVENTION

Figure 1:
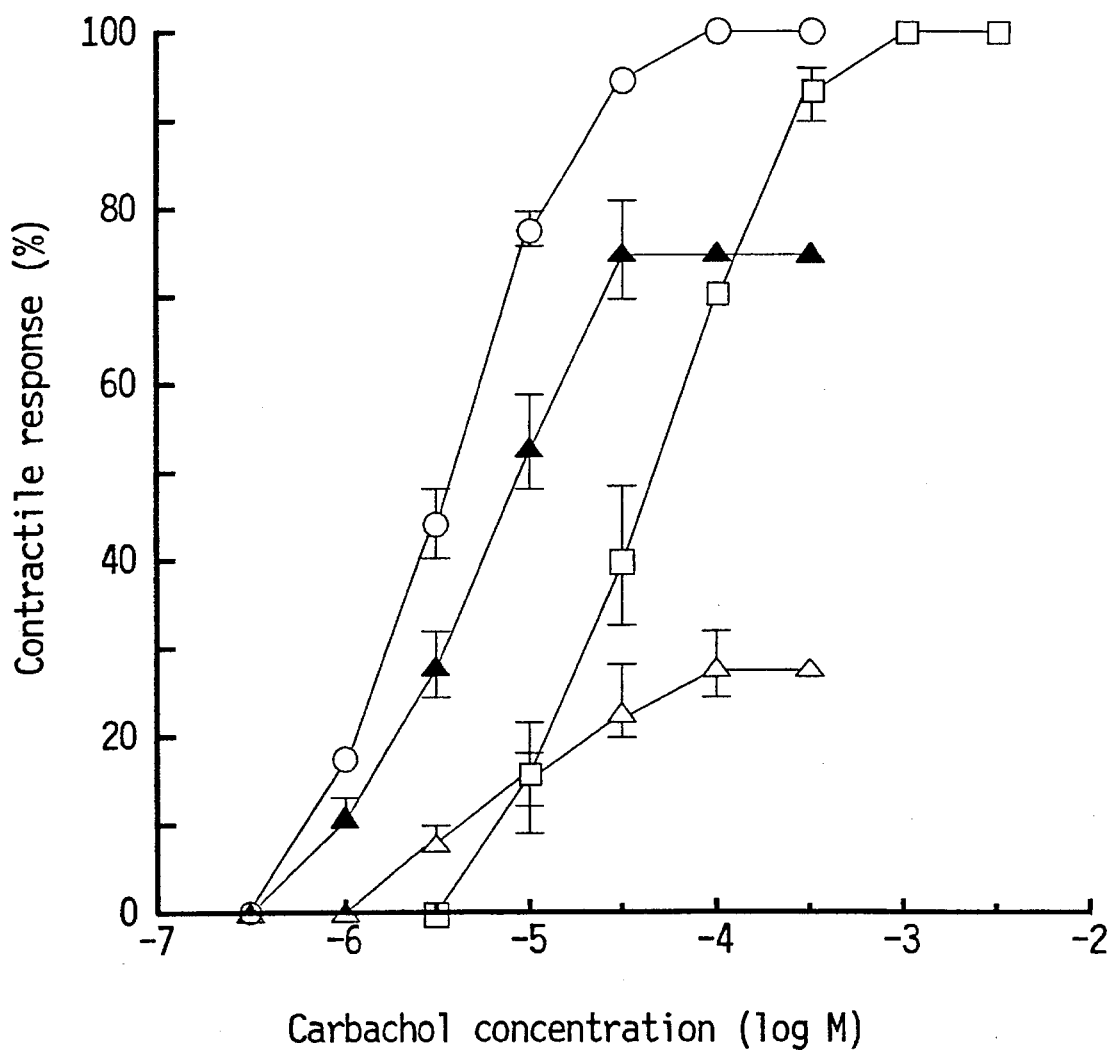
FIG. 1 is a graph showing concentration-response curves of carbachol after treating with AA-673 to be mentioned later or tropicamide, wherein the maximal contraction caused by carbachol alone is taken as 100%. In the Figure, the axis of abscissa indicates common logarithm (log M) of carbachol concentration (M) and the axis of ordinate indicates contractile response. In the Figure, ○ indicates a concentration-response curve of carbachol alone (n=8), and i is that after treatment for 5 min with $3 \times 10^{-5}$ M AA-673 (n=7), A is that after treatment for 5 rain with $10^{-4}$ M AA-673 (n=7) and □ is that after treatment for 5 min with $10^{-6}$ M tropicamide (n=6).

The alkyl represented by R in the formula (I)

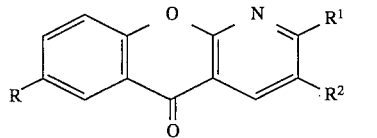

is preferably a straight or branched alkyl having 1 to 6 carbon atoms. Examples thereof include methyl, ethyl, n-propyl, isopropyl, n-butyl, isobutyl, sec-butyl, t-butyl, n-pentyl, isopentyl, neopentyl and n-hexyl. R is more preferably a straight or branched alkyl having 1 to 3 carbon atoms. Most particularly, R is isopropyl.

$R^1$ is hydrogen or amino.

$R^2$ is carboxyl. -COOH or tetrazole.

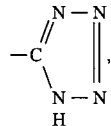

with preference given to carboxyl.

The physicochemical properties and production of the compound of the formula (I) wherein $R^2$ is carboxyl are described in detail in, for example, Japanese Patent Unexamined Publication No. 10587/1986.

In addition, the physicochemical properties and production of the compound of the formula (I) wherein $R^2$ is tetrazole are described in detail in, for example, Japanese Patent Unexamined Publication No. 48798/1979.

The compound (I) can be used as a pharmacologically acceptable salt. As such salt, there are exemplified salts with inorganic base, organic base, inorganic acid or organic acid such as basic or acidic amino acid.

Examples of the inorganic base include alkali metals such as sodium and potassium, alkaline earth metals such as calcium and magnesium, aluminum and ammonium.

Examples of the organic base include trimethylamine, diethylamine, triethylamine, pyridine, picoline, ethanolamine, diethanolamine, triethanolamine, dicyclohexylamine and N,N'-dibenzylethylenediamine.

Examples of the inorganic acid include hydrochloric acid, hydrobromic acid, nitric acid, sulfuric acid and phosphoric acid.

Examples of the organic acid include formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid.

Examples of the basic amino acid include arginine, lysine and ornithine.

Examples of the acidic amino acid include aspartic acid and glutamic acid.

These salts can be produced by a method known per se such as the method described in, for example, Japanese Patent Unexamined Publication No. 10587/1986 or an analogous method.

As is evident from the experimental examples to be mentioned later, the compound (I) and its salt have a superior relaxing action on the contraction of ciliary smooth muscle and can be used as a composition for the prophylaxis and treatment of myopia.

The composition for the prophylaxis and treatment of myopia of the present invention can be administered safely to mammals such as human, rabbit, dog, cat, cow, horse, monkey etc. by an oral or parenteral route.

The composition for the prophylaxis and treatment of myopia of the present invention can be produced by, for example, mixing the compound (I) or its salt with pharmaceutically acceptable carriers.

Examples of the pharmaceutically acceptable carrier include various organic or inorganic carriers which are conventionally used as preparation materials. For the production of solid preparations, excipient, lubricant, binder, disintegrator etc. may be used as appropriate and solvent, solubilizing agent, suspending agent, thickener, isotonizing agent, buffer, analgesic agent etc. may be used as appropriate for liquid preparations were necessary, additives for preparations, such as preservative, chelating agent, antioxidant, coloring, sweetener, flavor, aromatic etc. may be used according to a conventional method.

Suitable examples of the exicipient include lactose, sucrose, mannitol, starch, crystalline cellulose and light silicic acid anhydride.

Suitable examples of the lubricant include magnesium stearate, calcium stearate, talc and colloidal silica.

Suitable examples of the binder include sucrose, mannitol, multitol, starch, gelatin, gum arabic, tragacanth gum, crystalline cellulose, dextrin, hydroxypropylcellulose, hydroxypropylmethylcellulose, polyvinylpyrrolidone, sodium arginate, chitin and chitosan.

Suitable examples of the disintegrator include starch, carboxymethylcellulose, calcium carboxymethylcellulose, Carmellose sodium, sodium carboxymethyl starch, chitin and chitosan.

Suitable examples of the solvent include injectable water, alcohol (e.g., ethanol), propylene glycol, macrogol, glycerine, olive oil, sesame oil, peanut oil, cottonseed oil, castor oil and corn oil.

Suitable examples of the solubilizing agent include polyvinylpyrrolidone, cyclodextrin, caffeine, polyethylene glycol, propylene glycol, mannitol, benzyl benzoate, ethanol, trisaminomethane, cholesterol, triethanolamine, sodium carbonate and sodium citrate.

Suitable examples of the suspending agent include stearyl triethanolamine, sodium lauryl sulfonate, lauryl aminopropionate, lecithin, benzalkonium chloride, benzetonium chloride, monostearate glycerin, surfactants such as Polysorbate 80, and hydrophilic polymer such as polyvinyl alcohol, polyvinylpyrrolidone, sodium carboxymethylcellulose, methylcellulose, hydroxymethylcellulose, hydroxyethylcellulose, hydroxypropylcellulose, hydroxypropylmethylcellulose, gum arabic, gelatin and albumin.

Suitable examples of the thickener include egg yolk lecithin, gelatin, gum arabic, tragacanth gum, methylcellulose, sodium carboxymethylcellulose, hydroxyethylcellulose, hydroxypropylcellulose, polyvinyl alcohol, sodium polyacrylate, sodium arginate and pectine.

Suitable examples of the isotonizing agent include sorbitol, glycerin, polyethylene glycol, propylene glycol, glucose and sodium chloride.

Suitable examples of the buffer include phosphate buffer, borate buffer, citrate buffer, tartrate buffer and acetate buffer.

Suitable examples of the analgesic agent include benzyl alcohol.

Suitable examples of the preservative include p-hydroxybenzoic acid esters, sodium tetraborate, chlorobutanol, benzyl alcohol, phenethyl alcohol, dehydroacetic acid, sorbic acid and its salt, p-chloromethaxynol, chlorocresol and thimerosal.

Suitable examples of the chelating agent include sodium edetate, sodium citrate and condensed sodium phosphate.

Suitable examples of the antioxidant include sulfite, ascorbic acid, $\alpha$-tocopherol and cysteine.

Suitable examples of the coloring include tar color, licorice extract, riboflavin and zinc oxide.

Suitable examples of the sweetener include glucose, sucrose, fructose, honey, saccharin and licorice.

Suitable examples of the flavor include vanillin, menthol and rose oil.

Suitable examples of the aromatic include fennel oil, borneol and menthol.

In addition to the above-mentioned, pharmaceutically acceptable carriers include agar, casein and collagen.

Moreover, other drug for the prevention and treatment of myopia such as methyl neostigminesulfate, tropicamide or a drug containing these as active ingredients, and components having other efficacy may be added as appropriate.

The pH of the composition for the prophylaxis and treatment of myopia of the present invention as an aqueous solution is preferably from 4 to 9 in view of the stability of the compound (I) and its salt.

The oral preparation includes solid preparations such as powder, granule, tablet and capsule, and liquid preparations such as emulsion, syrup and suspension.

Tablets are produced by adding the aforementioned excipient, disintegrator, binder, lubricant etc. as appropriate to the compound (I) or its salt and press-forming the mixture into tablets. Subsequent to the press-forming, the aforementioned sweetener, flavor, aromatic etc. may be further added as desired or coating may be applied by a method known per se for enteric coating or sustained release of the drug. The usable coating agents are, for example, hydroxypropylcellulose, hydroxypropylmethylcellulose, cellulose acetate phthalate, hydroxypropylmethylcellulose phthalate, hydroxypropylmethylcellulose acetate succinate and ethylcellulose.

A suspension can be produced, for example, by suspending the compound (I) or its salt in the aforementioned solvent. In doing so, the aforementioned suspending agent may be used on demand.

The parenteral preparation includes, for example, injection and preparation for local administration to the eye.

The injection includes subcutaneous injection, intravenous injection and intramuscular injection. The injection may be aqueous or non-aqueous and may be either a solution or a suspension.

The preparation for local administration to the eye includes, for example, eye drop, eye ointment and gel, with preference given to eye drop. Eye drop may be aqueous or non-aqueous and may be either a solution or a suspension.

The composition for the prophylaxis and treatment of myopia of the present invention is preferably used as a preparation for local administration to the eye, particularly as an eye drop, more particularly an aqueous eye drop.

Injections can be produced by, for example, dissolving the compound (I) or its salt in injectable water together with the aforementioned preservative, isotonizing agent etc. when an aqueous injection is desired, and by dissolving or suspending same in propylene glycol, olive oil, sesame oil or cottonseed oil when an oily injection is desired.

The aqueous eye drop can be produced by, for example, heating purified water, dissolving a preservative therein, adding a solubilizing agent, adding the compound (I) or its salt and completely dissolving the added ingredients. Along therewith, buffer, isotonizing agent, chelating agent, thickener etc. may be used.

Preferable solubilizing agent is polyvinylpyrrolidone, cyclodextrin or caffeine, with particular preference given to polyvinylpyrrolidone. When polyvinylpyrrolidone is used, the solubility of the compound (I) and its salt can be greatly improved and the stability of the compound (I) and its salt can be remarkably enhanced.

For example, polyvinylpyrrolidone preferably used has an average molecular weight of from about 25000 to about 120000, preferably about 40000. The amount of polyvinylpyrrolidone added is generally from 0.2 to 20 (W/V) %, preferably from 0.5 to 15 (W/V) %, and particularly preferably from 1 to 10 (W/V) %.

The buffer is preferably a borate buffer. When a borate buffer is used, a liquid preparation with less irritation can be obtained as compared with when other buffer such as a phosphate buffer is used. In this case, boric acid is added in a proportion of from 0.2 to 4 (W/V) %, preferably from 0.5 to 2 (W/V) %.

An aqueous eye drop suspension can be produced by adding, besides the additives used for the aforementioned aqueous eye drop, the above-mentioned suspending agent as appropriate.

The pH of the above-mentioned aqueous eye drop and aqueous eye drop suspension is preferably from 4 to 9, particularly preferably from 5 to 8.

A non-aqueous eye drop can be produced by, for example, dissolving or suspending the compound (I) or its salt in a water-soluble solvent such as alcohol (e.g., ethanol), propylene glycol, macrogol, glycerinpropylene glycol, ethanol or glycerin, or an oily solvent such as olive oil, sesame oil, peanut oil, cottonseed oil, castor oil or corn oil.

An eye ointment can be produced, for example, by appropriately using vaseline, plastibase or liquid paraffin as a base material.

A gel for the eye can be produced by, for example, using carboxyvinyl polymer, ethylene maleic anhydride polymer, polyoxyethylene-polyoxypropylene block copolymer or gum gelanic as appropriate as a base material.

While the dose of the composition for the prophylaxis and treatment of myopia of the present invention varies depending on administration route, symptom, age, body weight of patients etc., the compound of the formula (I) or its salt is generally administered in an amount of from 0.01 to 500 mg/day for an adult. For example, the compound of the formula (I) or its salt as an active ingredient of an aqueous eye drop is administered at a dose of from 0.05 to 2 (W/V) %, preferably from 0.1 to 1 (W/V) % by one to several drops per administration once to several times, preferably 2 to 5 times a day according to the symptom.

The present invention is explained in detail by way of examples and experimental examples in the following so as to clarify the effects of the composition of the present invention. It should be noted that the following examples are for exemplary purposes only and do not limit the scope of the present invention. In the following description, the compound of the formula (I) wherein R is isopropyl, $R^1$ is amino and $R^2$ is carboxyl is referred to simply as AA-673 and the compound wherein R is isopropyl, $R^1$ is hydrogen and $R^2$ is tetrazole is referred to simply as T-19465.

Example 1

Aqueous eye drop

| Formulation | |
|---|---|
| AA-673 | 5 g |
| Boric acid | 16 g |
| Sodium tetraborate | 10 g |
| Polyvinylpyrrolidone (average molecular weight 40000) | 20 g |
| Caffeine | 2 g |
| Polyethylene glycol (average molecular weight 4000) | 5 g |
| Methyl p-hydroxybenzoate | 0.26 g |
| Propyl p-hydroxybenzoate | 0.14 g |
| Sterile purified water to make the total amount | 1000 ml (pH 6.0) |

Preparation

Sterile purified water (800 ml) was heated and methyl p-hydroxybenzoate and propyl p-hydroxybenzoate were dissolved therein, followed by sequential dissolution therein of boric acid, sodium tetraborate, polyvinylpyrrolidone (average molecular weight 40000), caffeine, polyethylene glycol and AA673. After cooling, sterile purified water was added thereto to make the total amount 1000 ml, which was then sterilized by filtration through a 0.22 μm membrane filter and filled in a predetermined container to give an aqueous eye drop.

Example 2

Aqueous eye drop

| Formulation | |
|---|---|
| AA-673 | 2.5 g |
| Boric acid | 16 g |
| Sodium tetraborate | 7 g |
| Polyvinylpyrrolidone (average molecular weight 4000) | 20 g |
| Methyl p-hydroxybenzoate | 0.26 g |
| Propyl p-hydroxybenzoate | 0.14 g |
| Sterile purified water to make the total amount | 1000 ml (pH 7.5) |

Preparation

Sterile purified water (800 ml) was heated and methyl p-hydroxybenzoate and propyl p-hydroxybenzoate were dissolved therein with heating. The obtained solution was allowed to cool to room temperature. Boric acid, sodium tetraborate and polyvinylpyrrolidone, and then AA-673 were dissolved therein. Sterile purified water was added thereto to make the total amount 1000 ml, which was then sterilized by filtration through a 0.22 μm membrane filter and filled in a predetermined container to give an aqueous eye drop.

Example 3

Aqueous eye drop suspension

| Formulation | |
|---|---|
| AA-673 | 10 g |
| Sodium dihydrogenphosphate | 50 g |
| Sodium chloride | 9 g |
| Polysorbate 80 | 20 g |
| Chlorobutanol | 3 g |
| Sodium hydroxide | appropriate amount |
| Sterile purified water to make the total amount | 1000 ml (pH 5.0) |

Preparation

Sterile purified water (800 ml) was heated and chlorobutanol was dissolved therein, followed by sequential dissolution of sodium dihydrogenphosphate, sodium chloride and Polysorbate 80. The solution was allowed to cool to room temperature. The obtained solution was adjusted to pH 5.0 with sodium hydroxide, and sterile purified water was added thereto to make the total amount 1000 ml, which was then sterilized by filtration through a 0.22 μm membrane filter. AA-673 sterilized in advance was homogeneously dispersed therein to give an aqueous eye drop suspension.

Example 4

Oily eye drop

| Formulation | |
|---|---|
| AA-673 | 20 g |
| Cottonseed oil to make the total amount | 1000 ml |

Preparation

AA-673 was added to cottonseed oil sterilized in advance to give an oily eye drop.

Example 5

Eye ointment

| Formulation | |
|---|---|
| AA-673 | 10 g |
| Liquid paraffin | 100 g |
| White vaseline to make the total amount | 1000 g |

Preparation

Liquid paraffin and white vaseline were sterilized by heating in advance. AA-673 was thoroughly triturated with the liquid paraffin and kneaded well with the white vaseline to give an eye ointment.

Example 6

Gel

| Formulation | |
|---|---|
| AA-673 | 5 g |
| Carboxyvinyl polymer | 10 g |
| Phenethyl alcohol | 5 g |
| Sodium hydroxide | appropriate amount |
| Sterile purified water to make the total amount | 1000 g (pH 7.0) |

Preparation

Phenethyl alcohol was dissolved in sterile purified water (800 ml) and the solution was sterilized by filtration through a 0.22 μm membrane filter. AA-673 sterilized in advance was suspended in this solution and sterile carboxyvinyl polymer was added thereto with vigorous shaking for dissolution. The obtained solution was adjusted to pH 7.0 with sodium hydroxide and added with sterile purified water to make the total amount 1000 g, whereby a gel was prepared.

Example 7

Tablet

| Formulation | |
|---|---|
| AA-673 | 10 mg |
| Lactose | 35 mg |
| Corn starch | 150 mg |
| Crystallite cellulose | 30 mg |
| Magnesium stearate | 5 mg |
| | 230 mg per tablet |

Preparation

AA-673, lactose, corn starch, crystallite cellulose (⅔ amount) and magnesium stearate (½ amount) were admixed and granulated. The remaining amounts of crystallite cellulose and magnesium stearate were added to the obtained granules. The mixture was press-formed to give tablets.

Example 8

Capsule

| Formulation | |
|---|---|
| AA-673 | 10 mg |
| Lactose | 90 mg |
| Crystallite cellulose | 70 mg |
| Magnesium stearate | 10 mg |
| | 180 mg per capsule |

Preparation

AA-673, lactose, crystallite cellulose and magnesium stearate (½ amount) were admixed and granulated. The remaining amount of magnesium stearate was added to the obtained granules and the mixture was sealed in a gelatin capsule to give a capsule.

Example 9

Injection

| Formulation | |
|---|---|
| AA-673 | 10 mg |
| Inositol | 100 mg |
| Benzyl alcohol | 20 mg |
| | 130 mg per ampoule |

Preparation

AA-673, Inositol and benzyl alcohol were dissolved in injectable distilled water to make the total amount 2 ml and the solution was sealed in an ampoule. The entire step was carried out aseptically.

Experimental Example 1

Antagonistic action of AA-673 on carbachol-induced contraction of ciliary smooth muscle of pigmented rabbits Test materials Male pigmented rabbits (Dutch) weighing about 2 kg were used as test animals. As the test drugs, used were carbachol ($3\times10^{-7}$ M-$3\times10^{-3}$ M) having contracting action on ciliary smooth muscle, AA-673 ($10^{-6}$ M-$10^{-3}$ M) and tropicamide ($10^{-7}$ M-$3\times10^{-5}$ M) [active ingredient of Mydrin-M (trade mark, a mydriatic and cycloplegic manufactured by SANTEN PHARMACEUTICAL CO., LTD., Osaka, Japan)] having muscarine receptor antagonistic action. The figures in parentheses indicate final drug concentrations, hereinafter the same.

Test method

Preparation of ciliary smooth muscle: The eyeballs of pigmented rabbits were removed and the posterior part thereof was cut away and the anterior part thereof was divided into two. From one of them were removed vitreous body and lens, and iris was cut apart. Then, ciliary smooth muscle was gently peeled off from sclera to give 1 mm wide, 10 mm long muscle preparations. Measurement: The muscle preparations were suspended in a 10 ml organ bath filled with Krebs-Ringer solution aerated with 95% $O_2$-5% $CO_2$ and kept at 37° C. The response to the drugs was recorded isometrically under the resting tension of about 30

Figure 2:
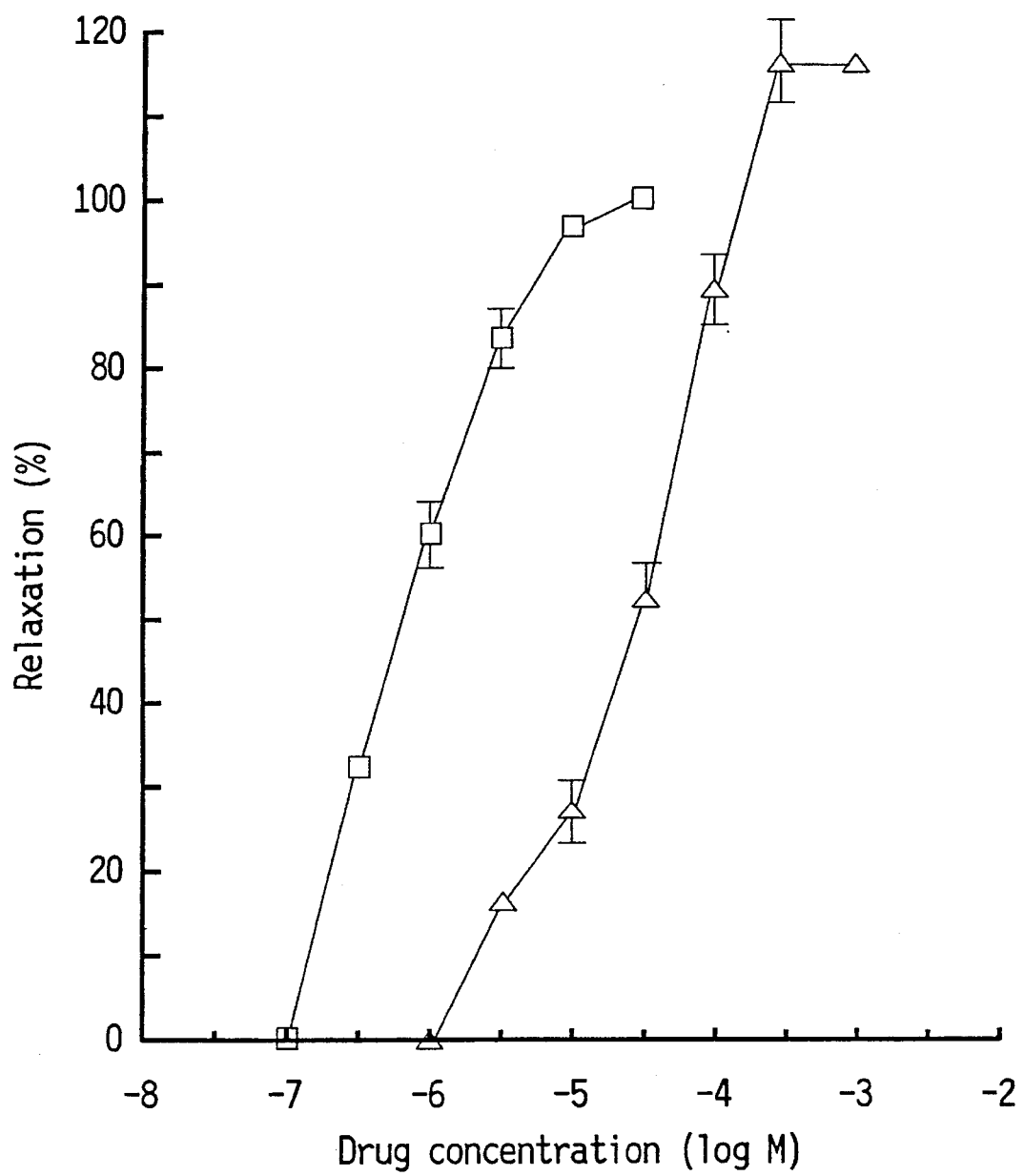
FIG. 2 shows relaxation of carbachol ($3 \times 10^{-5}$ M)-induced tonic contraction by AA-673 or tropicamide, wherein the difference between the maximal tonic contraction and resting tension is taken as 100%. In the Figure, the axis of abscissa indicates common logarithm (log M) of drug concentration (M) and the axis of ordinate indicates percent relaxation. In the Figure, Δ is AA-673 (n=7) and □ is tropicamide (n=7).

The inhibition of carbachol-induced phasic contraction by the treatment for 5 rain with AA-673 ($3\times10^{-5}$ M or $10^{-4}$ M) or tropicamide ($10^{-6}$ M) and relaxation of tonic contraction following the carbachol ($3\times10^{-5}$ M)-induced phasic contraction, by AA-673 ($10^{-6}$ M-$10^{-3}$ M) or tropicamide ($10^{-7}$ M-$3\times10^{-5}$ M) are respectively shown in FIG. 1 and FIG. 2.

Results (1) The ciliary smooth muscle of rabbit showed concentration-dependent contraction by $10^{-6}$ M-$10^{-4}$ M carbachol (vide FIG. 1).

(2) Tropicamide ($10^{-6}$ M) caused parallel shift of concentration-response curve of carbachol toward the high concentration side. That is, tropicamide is a competitive antagonist (vide FIG. 1).

AA-673 at a concentration of $3\times10^{-5}$ M inhibited about 25% of the maximal contraction (100%) induced by carbachol, and about 70% at a concentration of $10^{-4}$ M. In view of the inhibition of the maximal contraction induced by carbachol, AA-673 is considered a non-competitive antagonist (vide FIG. 1).

(3) Tropicamide at a concentration of not less than $3\times10^{-7}$ M relaxed the tonic contraction induced by carbachol ($3\times10^{-5}$ M) in a concentration-dependent manner, whereas it failed to relax the contraction to a level below the resting tension (the relaxation of the maximal tonic contraction to the resting tension was taken as 100%) (vide FIG. 2).

AA-673 at a concentration of not less than $3\times10^{-6}$ M relaxed the tonic contraction induced by carbachol ($3\times10^{-5}$ M) in a concentration-dependent manner. AA-673, moreover, relaxed the contraction to a level below (116%) the resting tension (vide FIG. 2).

From these results, it is now indicated that AA-673 has relaxing action on ciliary smooth muscle of rabbits. Tropicamide, which is the active ingredient of Mydrin-M, showed inhibition of phasic contraction and relaxation of the subsequent tonic contraction induced by carbachol, and so did AA-673. Tropicamide shows competitive antagonistic action against carbachol which has the similar action with acetylcholine–a neuronal substance contracting ciliary smooth muscle–at the nerve terminal receptor. In contrast, AA-673 does not show competitive antagonistic action against carbachol at the nerve terminal receptor but possibly causes relaxation by acting directly on ciliary smooth muscle according to a different mechanism. Therefrom it follows that AA-673 may relax contraction of ciliary smooth muscle due to a different nerve transmitting substance besides acetylcholine. If myopia is caused by the contraction due to a substance besides acetylcholine, AA-673 will be a promising substance for the prophylaxis and treatment of myopia.

Experimental Example 2

Effects of the composition for prophylaxis and treatment of myopia of the present invention on the patients with myopia who did not regain visual acuity by the administration of Mydrin-M or Miopin To 5 patients with myopia who did not regain visual acuity by the administration of Mydrin-M or Miopin (trade mark, an accommodation improver containing methyl neostigminesulfate as an active ingredient, manufactured by SANTEN PHARMACEUTICAL CO., LTD., Osaka, Japan) was administered the aqueous eye drop (hereinafter briefly referred to as the agent) obtained in Example 2 and the effects of the composition for prophylaxis and treatment of myopia of the present invention was evaluated.

With regard to 5 patients (patients A to E in Table 1 ranging from 9 years old to 28 years old) who were allegedly failing in eyesight, visual power without glasses (right and left) and refractive error (right and left) [measured with autorefractometer, unit: D (diopter)] were measured. The results are shown in Table 1. The length of the axis of the eye and corneal curvature radius of the 5 patients were within the normal range.

Miopin was instilled 3 or 4 times a day by one drop and one drop of Mydrin-M was instilled before going to bed to the both eyes of the patients A to E for 3 months. Visual power without glasses (right and left) and refractive error (right and left) of the patients A to E were measured at 3 months from the initial visit to the hospital, the results of which are shown in Table 1. As is apparent from Table 1, the five patients scarcely showed diversity in visual power without glasses and refractive error, exhibiting no effects of prophylaxis and treatment of myopia.

Then, the agent of the present invention was instilled instead of Miopin 3 or 4 times a day by one drop and one drop of Mydrin-M was instilled before going to bed to the both eyes of the patients A to E for 3 months. Visual power without glasses (right and left) and refractive error (right and left) of the patients A to E were measured at 3 months thereafter (i.e., 6 months from the initial visit to the hospital), the results of which are shown in Table 1. As is apparent from Table 1, the five patients showed recovery in eyesight without glasses to not less than 1.0 and apparent improvements in refractive error.

TABLE 1

| pa-tient | age | sex | drug (administered period) | visual power w/o glasses | | refractive error | |
|---|---|---|---|---|---|---|---|
| | | | | right | left | right | left |
| A | 11 | male | None (initial visit to the hospital) | 0.6 | 0.6 | −1.5 | −1.5 |
| | | | Mydrin-M + Miopin (3 mon) | 0.6 | 0.5 | −1.5 | −1.75 |
| | | | Mydrin-M + agent of Example 2 (3 mon) | 1.0 | 0.9 | +0.25 | +0.5 |
| B | 9 | female | None (initial visit to the hospital) | 0.7 | 0.7 | −1.75 | −1.5 |
| | | | Mydrin-M + Miopin (3 mon) | 0.7 | 0.5 | −1.5 | −1.75 |
| | | | Mydrin-M + agent of Example 2 (3 mon) | 1.0 | 1.0 | −0.25 | −0.25 |
| C | 15 | female | None (initial visit to the hospital) | 0.4 | 0.5 | −2.5 | −2.75 |
| | | | Mydrin-M + Miopin (3 mon) | 0.5 | 0.5 | −2.25 | −2.0 |
| | | | Mydrin-M + agent of Example 2 (3 mon) | 1.0 | 1.0 | −0.5 | −0.5 |
| D | 28 | male | None (initial visit to the hospital) | 0.3 | 0.2 | −2.0 | −1.75 |
| | | | Mydrin-M + Miopin (3 mon) | 0.4 | 0.3 | −1.75 | −2.0 |
| | | | Mydrin-M + agent of Example 2 (3 mon) | 1.0 | 1.2 | −0.5 | −0.25 |
| E | 13 | male | None (initial visit to the hospital) | 0.6 | 0.4 | −2.75 | −2.0 |
| | | | Mydrin-M + Miopin (3 mon) | 0.5 | 0.5 | −2.5 | −2.0 |
| | | | Mydrin-M + agent of Example 2 (3 mon) | 1.5 | 1.2 | −0.75 | −0.5 |

From these results, it was found that the agent of the present invention, when combinedly used with Mydrin-M, was effective for the prophylaxis and treatment of myopia of the patients who failed to show improvements by the combined use of Miopin and Mydrin-M which are the conventional preparations for the prophylaxis and treatment of myopia. Accordingly, the usefulness of the agent of the invention for the prophylaxis and treatment of myopia was suggested.

Experimental Example 3

Effects of the agent of the present invention for the prophylaxis and treatment of myopia on patients with myopia The agent of the present invention was administered to 5 patients with myopia and the effects of the agent for the prophylaxis and treatment of myopia was examined.

With regard to five patients (patients F to J in Table 2, ranging from 9 years old to 28 years old) who were allegedly failing in eyesight, visual power without glasses (right and left) and refractive error (right and left) [measured with autorefractometer, unit: D (diopter)] were measured. The results are shown in Table 2. The length of the axis of the eye and corneal curvature radius of the five patients were within the normal range.

The agent of the present invention was instilled 3 or 4 times a day by one drop to the both eyes of the patients F to J for 3 months. Visual power without glasses (right and left) and refractive error (right and left) of the patients F to J were measured 3 months thereafter, the results of which are shown in Table 2. As is apparent from Table 2, the five patients showed recovery of eyesight without glasses to not less than 1.0 and apparent improvements in refractive error.

Test animal

Two male cynomolgus monkeys weighing about 3 kg were used as test animals. As test drugs, used were carbachol which causes myopia by contracting ciliary smooth muscle to change the power of the lens, phenylephrine [the active ingredient of Neosynesin (trade mark, a mydriatic manufactured by KOWA. COMPANY, LTD., Japan)] which stimulates α-receptor to cause mydriasis by contracting dilator smooth muscle, and the experimental drug AA-673.

Test method

TABLE 2

| pa-tient | age | sex | drug (administered period) | visual power w/o glasses | | refractive error | |
|---|---|---|---|---|---|---|---|
| | | | | right | left | right | left |
| F | 14 | male | None (initial visit to the hospital) | 0.4 | 0.5 | −1.75 | −1.5 |
| | | | Agent of Example 2 (3 mon) | 1.0 | 1.2 | −0.25 | +0.25 |
| G | 9 | male | None (initial visit to the hospital) | 0.6 | 0.7 | −0.75 | −0.75 |
| | | | Agent of Example 2 (3 mon) | 1.2 | 1.5 | +0.25 | +0.25 |
| H | 28 | male | None (initial visit to the hospital) | 0.3 | 0.2 | −2.75 | −2.5 |
| | | | Agent of Example 2 (3 mon) | 1.0 | 1.0 | −0.5 | −0.25 |
| I | 12 | female | None (initial visit to the hospital) | 0.6 | 0.7 | −1.75 | −2.0 |
| | | | Agent of Example 2 (3 mon) | 1.0 | 1.2 | −0.25 | +0.25 |
| J | 18 | female | None (initial visit to the hospital) | 0.6 | 0.5 | −1.75 | −2.0 |
| | | | Agent of Example 2 (3 mon) | 1.0 | 1.0 | −0.5 | −0.75 |

In view of the fact that the patients used in the experimental examples of the present invention had the length of the axis of the eye within the normal range and showed no change of corneal curvature radius, they were considered to have refractive myopia which is caused by the tension (contraction) of ciliary smooth muscle. Accordingly, it was suggested that the agent of the present invention was effective for the prophylaxis and treatment of myopia of patients with myopia, due to the relaxation of the contraction of the ciliary smooth muscle. To conclude, the agent of the present invention showed superior effects in the prophylaxis and treatment of myopia, and it was useful as an agent for the prophylaxis and treatment of myopia.

Experimental Example 4

Effects of AA-673 on acute refractive myopia of monkeys, which is induced by instillation of carbachol Carbachol (0.75%) was instilled in the both eyes at 30 minute intervals and refractive error was measured with time. The measurement was done before carbachol instillation and at 15-minute intervals starting from 30 minutes after the first carbachol instillation and until the pupil diameter became not more than ca. 1 mm, at which level, the measurement was unattainable. AA-673 (experimental drug) was instilled in one eye and physiological saline was instilled in the other eye 4 times at 5-minute intervals starting from 90 minutes before the carbachol instillation. With the aim of maintaining mydriasis for refractive error measurement, 5% phenylephrine was instilled in the both eyes 6 times at 5-minute intervals starting from 120 minutes before the carbachol instillation. Every drug was instilled by 20 μl.

The protocol was as follows:

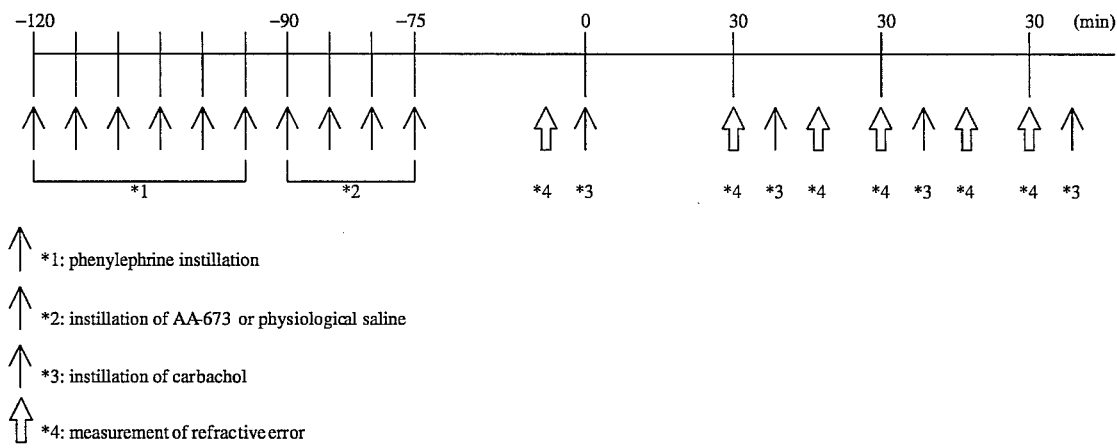

*1: phenylephrine instillation

*2: instillation of AA-673 or physiological saline

*3: instillation of carbachol

*4: measurement of refractive error

Result

Figure 3:
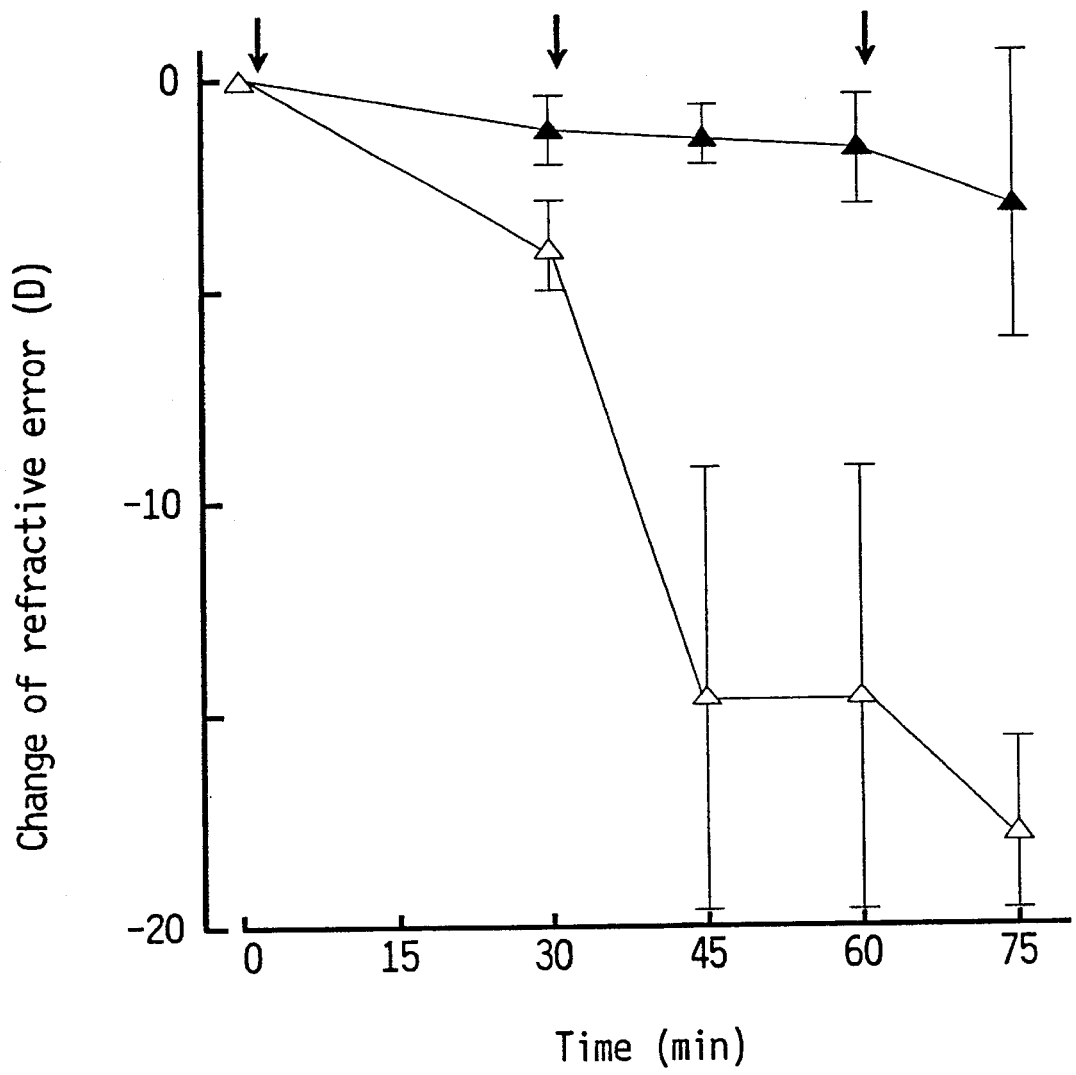
FIG. 3 is a graph showing the changes of refractive error after the instillation of carbachol. In the Figure, the axis of abscissa indicates time (min) after the first instillation of carbachol. The axis of ordinate indicates the changes (D) based on the initial refractive error (immediately before the instillation of carbachol). In the Figure, Δ indicates the refractive error of the eye instilled with physiological saline, ▲ indicates the refractive error of the eye instilled with AA-673 and ↓ indicates instillation of carbachol. Each value shows average changes of refractive error and standard error of two animals.

Myopia of 15D was found in the eye instilled with physiological saline from 15 minutes after the second instillation of carbachol. In contrast, the eye instilled with 1% AA-673 showed no change in refractive error. When carbachol was instilled 2 more times, myopia proceeded in the eye instilled with physiological saline, whereas AA-673 almost completely inhibited the development of myopia (vide FIG. 3).

The above result is in harmony with the result that the carbachol-induced contraction was antagonized by AA-673 in ciliary smooth muscle of rabbit. Accordingly, the effect demonstrated in the present model is considered to be attributable to the inhibition of carbachol-induced contraction and relaxation of ciliary smooth muscle by AA-673. It is suggested, therefore, that AA-673 is effective on refractive myopia wherein ciliary smooth muscle is in a contractive state.

Experimental Example 5

Antagonistic action of T-19465 on carbachol-induced contraction of ciliary smooth muscle of pigmented rabbits Test materials As the test animals, used were male pigmented rabbits (Dutch) weighing about 2 kg. As the test drugs, used were carbachol ($3\times10^{-7}$ M-$10^{-4}$ M) and T-19465 ($10^{-6}$-$3\times10^{-4}$ M). The figures in parentheses indicate final drug concentrations.

Test method

Preparation of ciliary smooth muscle: The eyeballs of the pigmented rabbits were removed and the posterior part thereof was cut away and the anterior part thereof was divided into two. From one of them were removed vitreous body and lens, and iris was cut apart. Then, ciliary smooth muscle was gently peeled off from sclera to give 1 mm wide, 10 mm long muscle preparations.

Measurement

The muscle preparations as prepared above were suspended in a 10 ml organ bath filled with Krebs-Ringer solution aerated with 95% $O_2$-5% $CO_2$ and kept at 37° C. The response to the drugs was recorded isometrically under the resting tension of about 30 mg.

Figure 4:
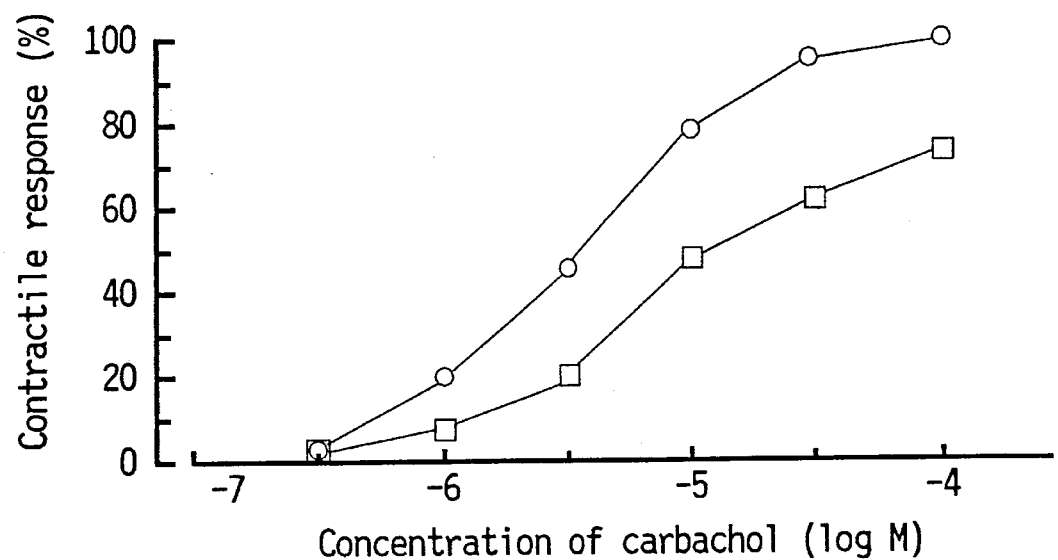
FIG. 4 is a graph showing concentration-response curves of carbachol after treatment with T-19465 to be mentioned later. In the Figure, the axis of abscissa indicates common logarithm (log M) of carbachol concentration (M) and the axis of ordinate indicates contractile response. In the Figure, ○ indicates concentration-response curve of carbachol alone and □ is that after treatment for 5 min with $10^{-4}$ M T-19465.
Figure 5:
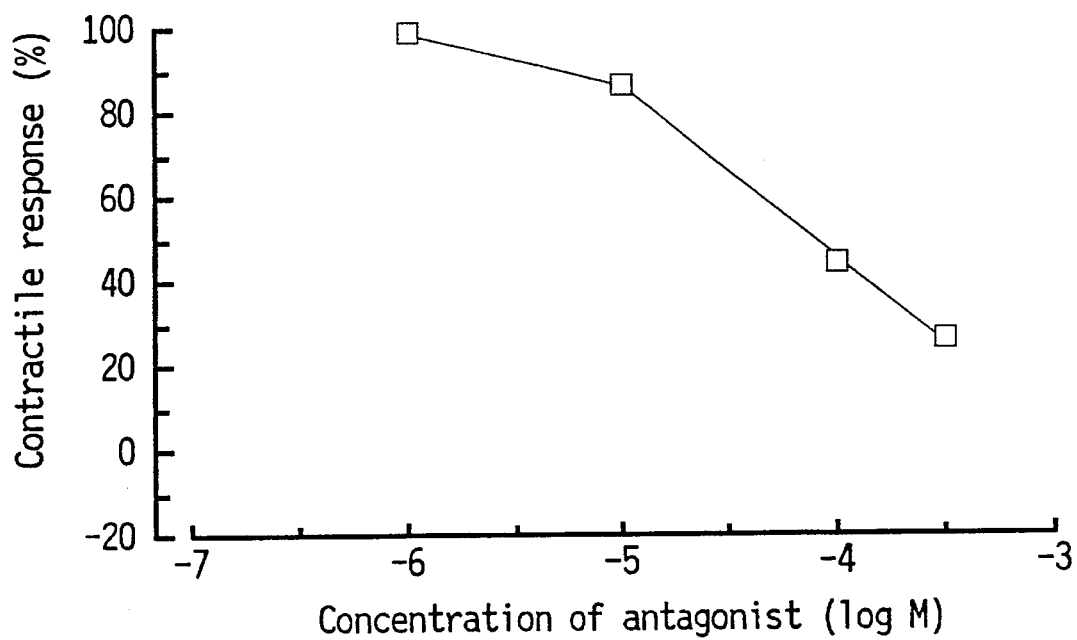
FIG. 5 is a graph showing relaxation of carbachol ($3 \times 10^{-5}$)-induced tonic contraction, by T-19465. In the Figure, the axis of abscissa indicates common logarithm (log M) of T-19465 concentration (M) and the axis of ordinate indicates contractile response.

The inhibition of carbachol-induced phasic contraction by 5 min treatment with $10^{-4}$ M T-19465 and relaxation of tonic contraction following the carbachol ($3\times10^{-5}$ M)-induced phasic contraction, by T-19465 ($10^{-6}$-$3\times10^{-4}$ M) are shown in FIG. 4 and FIG. 5, respectively.

Results

The concentration-response curves of carbachol are shown in FIG. 4. The treatment for 5 minutes with $10^{-4}$ M T-19465 resulted in the inhibition of the carbachol-induced contraction and about 28% inhibition of the maximal carbachol-induced contraction. However, the concentration-response range of carbachol-induced contraction was not affected.

FIG. 5 shows the relaxation of carbachol-induced tonic contraction by T-19465. The result reveals that $3'10^{-4}$ M T-19465 relaxed the maximal carbachol-induced tonic contraction by about 72%.

The composition for the prophylaxis and treatment of myopia of the present invention not only shows relaxing action on the ciliary smooth muscle of rabbit, but also shows superior effects of prevention and treatment of myopia of the patients on whom Mydrin-M, a conventional preparation for the prophylaxis and treatment of myopia, failed to have effects. In addition, the composition does not show a mydriatic response and can be advantageously used for the prophylaxis and treatment of myopia.

What is claimed is:

1. A method for the treatment of myopia, comprising administering an effective amount of a compound of the formula (I)

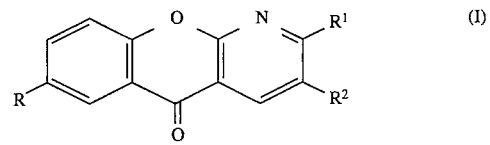

wherein R is an alkyl, $R^1$ is a hydrogen or an amino and $R^2$ is a carboxyl or a tetrazole, or a salt thereof to a patient suffering from myopia.

2. The method of claim 1, wherein R is an alkyl having 1 to 6 carbon atoms.

3. The method of claim 1, wherein R is an isopropyl.

4. The method of claim 1, wherein $R^1$ is an amino.

5. The method of claim 1, wherein $R^2$ is a carboxyl.

6. The method of claim 1, comprising administering a compound of the formula

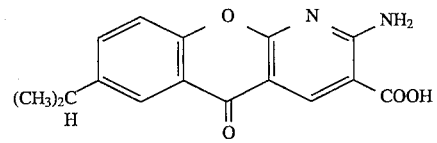

or a salt thereof as the compound of the formula (I) or the salt thereof.

7. The method of claim 1, comprising administering the compound of the formula (I) or a salt thereof to a local site in the eye.

8. The method of claim 7, comprising administering to a local site in the eye as an eye drop.

9. The method of claim 8, wherein the eye drop is an aqueous eye drop.

10. The method of claim 1, comprising a concurrent use of a solubilizing agent.

11. The method of claim 10, wherein the solubilizing agent is polyvinylpyrrolidone.

* * * * *